(12) United States Patent
Farina et al.

(10) Patent No.: US 11,421,182 B2
(45) Date of Patent: Aug. 23, 2022

(54) OIL EXTRACTION APPARATUS

(71) Applicants: Anthony J. Farina, Northport, NY (US); Chris Turner, Weston, FL (US)

(72) Inventors: Anthony J. Farina, Northport, NY (US); Chris Turner, Weston, FL (US)

( * ) Notice: Subject to any disclaimer, the term of this patent is extended or adjusted under 35 U.S.C. 154(b) by 0 days.

(21) Appl. No.: 17/547,646

(22) Filed: Dec. 10, 2021

(65) Prior Publication Data
US 2022/0213406 A1 Jul. 7, 2022

Related U.S. Application Data

(60) Provisional application No. 63/134,778, filed on Jan. 7, 2021.

(51) Int. Cl.
| | |
|---|---|
| *A01H 6/28* | (2018.01) |
| *B01J 19/10* | (2006.01) |
| *B01D 11/02* | (2006.01) |
| *B01D 11/00* | (2006.01) |
| *C11B 1/10* | (2006.01) |
| *A23L 33/105* | (2016.01) |

(52) U.S. Cl.
CPC ............... *C11B 1/106* (2013.01); *A01H 6/28* (2018.05); *A23L 33/105* (2016.08); *B01D 11/0261* (2013.01); *B01J 19/10* (2013.01); *C11B 1/108* (2013.01); *B01D 11/00* (2013.01); *B01D 11/02* (2013.01); *B01J 2219/00932* (2013.01)

(58) Field of Classification Search
CPC .......... B01J 2219/00932; B01D 11/00; B01D 11/02; B01D 11/0261
USPC ..................................................... 210/748.01
See application file for complete search history.

(56) References Cited

U.S. PATENT DOCUMENTS

| | | |
|---|---|---|
| 9,795,246 B1 | 10/2017 | Bellman et al. |
| 10,039,413 B1 | 8/2018 | Bellman et al. |
| 10,758,078 B2 | 9/2020 | Bellman et al. |
| 2018/0220836 A1 | 8/2018 | Bellman et al. |
| 2018/0303277 A1 | 10/2018 | Bellman et al. |
| 2019/0142209 A1 | 5/2019 | Bellman |
| 2020/0375390 A1 | 12/2020 | Bellman et al. |

*Primary Examiner* — Deborah D Carr
(74) *Attorney, Agent, or Firm* — Sean R. Wilsusen

(57) ABSTRACT

An oil extraction apparatus includes an ultrasonication vessel that receives raw plant material and ethanol. An ultrasonication probe ultrasonicates the raw plant material received in the ultrasonication vessel and generates a mixture including ultrasonicated raw plant material, plant oil, and ethanol. A collection vessel is in fluid communication with the ultrasonication vessel. The collection vessel receives a mixture including plant oil and ethanol from the ultrasonication vessel. A heater heats the collection vessel to separate ethanol from the mixture including plant oil and ethanol. A reclamation vessel is in fluid communication with the collection vessel. The reclamation vessel receives separated ethanol from the mixture including plant oil and ethanol. An ethanol collection tube is connected with the reclamation vessel. The ethanol collection tube is arranged to carry separated ethanol from the mixture including plant oil and ethanol to the reclamation vessel from the collection vessel.

18 Claims, 10 Drawing Sheets

OIL EXTRACTION APPARATUS

CROSS-REFERENCE TO RELATED APPLICATION

The present application claims priority to U.S. Provisional Patent Application No. 63/134,778, filed on Jan. 7, 2021, the entire contents of which are incorporated by reference herein.

TECHNICAL FIELD

This disclosure relates to an extraction apparatus and, more particularly, to an oil extraction apparatus and methods of using the same.

DISCUSSION OF RELATED ART

Consumers are increasingly purchasing and using various forms of hemp derived/cannabis products, and have been for thousands of years. Cannabidiol (CBD) oil is often associated with various health benefits, such as pain relief, and reduction of anxiety and depression. CBD oil is traditionally extracted from stalk, stems, leaves, or flowers of hemp material. Consumers may use a variety of forms of hemp derived/cannabis products, including CBD oil, for personal and/or medicinal use, among other uses.

Current extraction methods of oil take a significant amount of time and financial investment. For example, commercial extraction methods are expensive and require large volumes of industrial hemp and the use of solvents which may add unwanted toxins to CBD oil. There exists a need for extraction apparatuses and methods to provide consumers with an opportunity to safely create mixtures of their own desired concentration within a shorter amount of time.

Thus, an oil extraction apparatus may enable consumers to safely create their own mixtures in a timely fashion at their convenience.

SUMMARY

In accordance with an aspect of the disclosure, an oil extraction apparatus includes a heater assembly and a vessel. The vessel is configured to receive raw plant material and ethanol. The vessel is in contact with the heater assembly. An ultrasonic transducer is configured to ultrasonicate the raw plant material received in the vessel and generate a mixture including ultrasonicated raw plant material and ethanol. A pump is configured to transport the mixture. A filter is in fluid communication with the pump and receives the transported mixture. A coupling connection is between the vessel and the filter. A cooling assembly is in fluid communication with the vessel and a reclamation vessel. The reclamation vessel receives ethanol having passed through the cooling assembly from the vessel. The vessel is heated by the heater assembly to evaporate the ethanol received in the vessel through the coupling connection between the vessel and the filter and leave oil extracted from the ultrasonicated raw plant material in the vessel In some respects, the heater assembly is set to a temperature of approximately 60 degrees centigrade.

In some aspects, the extracted oil includes CBD oil.

In some aspects, stainless-steel tubing extends from the filter. The stainless-steel tubing may include a pressure-relief valve.

In some aspects, the cooling apparatus includes copper tubing and an aluminum cooling sleeve.

In some aspects, the cooling apparatus may include a Teflon® socket. The Teflon® socket is in fluid communication with the vessel.

In some aspects, the oil extraction apparatus may include an exhaust fan. The exhaust fan is configured to remove heat generated by the heater assembly.

In some aspects, the cooling assembly includes a plurality of aluminum cooling fans. The plurality of aluminum cooling fans are configured to circumferentially surround the copper tubing.

In some aspects, the ultrasonic transducer may be a probe.

In some aspects, the ultrasonic transducer is part of a quick-connect assembly. The quick-connect assembly is in fluid communication with the vessel.

In some respects, the pump is a peristaltic pump.

In some aspects, the reclamation vessel receives cooled ethanol having passed through the cooling assembly.

In some aspects, the vessel includes an air-tight lid. The air-tight lid may be removable.

In some aspects, the air-tight lid is in fluid communication with the cooling assembly.

In some aspects, a Polytetrafluoroethylene (PTFE) socket connects the vessel with the cooling assembly.

In some aspects, the oil extracted from the ultrasonicated raw plant material includes a whole spectrum CBD extract.

In some aspects, the oil extracted from the ultrasonicated raw plant material includes a broad spectrum CBD extract.

In accordance with an aspect of the disclosure, an oil extraction apparatus includes an ultrasonication vessel that receives raw plant material and ethanol. An ultrasonication probe is configured to be positioned in the ultrasonication vessel. The ultrasonication probe is configured to ultrasonicate the raw plant material received in the ultrasonication vessel and generate a mixture including ultrasonicated raw plant material, plant oil, and ethanol. A collection vessel is in fluid communication with the ultrasonication vessel. The collection vessel receives a mixture including plant oil and ethanol from the ultrasonication vessel. A heater heats the collection vessel to separate ethanol from the mixture including plant oil and ethanol. A reclamation vessel is in fluid communication with the collection vessel. The reclamation vessel receives separated ethanol from the mixture including plant oil and ethanol. An ethanol collection tube is connected with the reclamation vessel. The ethanol collection tube is arranged to carry separated ethanol from the mixture including plant oil and ethanol to the reclamation vessel from the collection vessel.

In some aspects, a sealing membrane is arranged between the ethanol collection tube and the collection vessel. The sealing membrane forms an airtight seal between the ethanol collection tube and the collection vessel.

In some aspects, the heater vaporizes ethanol in the mixture including plant oil and ethanol. The ethanol is carried through at least a portion of the ethanol collection tube as ethanol vapor.

In some aspects, a lift is arranged adjacent the collection vessel. The lift is configured to apply pressure between the collection vessel and the collection tube to form the aright seal between the collection tube and the collection vessel.

In some aspects, the heater includes a heating plate. The lift is configured to apply pressure to the heating plate to form the airtight seal between the collection tube and the collection vessel.

In some aspects, the lift is a mechanical lift or a hydraulic lift. The mechanical lift may be a scissor lift.

In some aspects, a cooling coil is arranged around at least a portion of the ethanol collection tube. The cooling coil is configured to convert ethanol vapor to liquid ethanol. The cooling coil may include copper or aluminum.

In some aspects, the ultrasonication vessel defines a cone shape.

In some aspects, a filter is arranged between the ultrasonication vessel and the collection vessel. The filter is configured to prevent ultrasonicated raw plant material from entering the collection vessel.

In some aspects, a check valve is arranged between the ultrasonication vessel and the collection vessel.

In some aspects, a housing is arranged between the ethanol collection tube and the collection vessel. The housing is configured to form an airtight seal between the collection tube and the collection vessel.

In some aspects, a lid of the oil extraction apparatus supports the ultrasonication probe. The ultrasonication probe can be removably positioned in the ultrasonication vessel by closing the lid and removed from the ultrasonication vessel by opening the lid.

In some aspects, the collection vessel includes an airtight lid. The airtight lid is configured to form an airtight seal between the collection vessel and the ethanol collection tube.

In accordance with an aspect of the disclosure, a method of oil extraction includes placing raw planter material and ethanol in an ultrasonication vessel. The raw plant material is ultrasonicated to generate a mixture including ultrasonicated raw plant material, plant oil, and ethanol. A mixture including plant oil and ethanol is transferred from the ultrasonication vessel to a collection vessel. The collection vessel is heated to separate ethanol from the mixture including plant oil and ethanol. The separated ethanol transferred from the collection vessel to a reclamation vessel to leave extracted plant oil in the collection vessel.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Descriptions of technical features or aspects of an exemplary embodiment of the disclosure should typically be considered as available and applicable to other similar features or aspects in another exemplary embodiment of the disclosure. Accordingly, technical features described herein according to one exemplary embodiment of the disclosure may be applicable to other exemplary embodiments of the disclosure, and thus duplicative descriptions may be omitted herein.

Exemplary embodiments of the disclosure will be described more fully below (e.g., with reference to the accompanying drawings).

Figure 1:
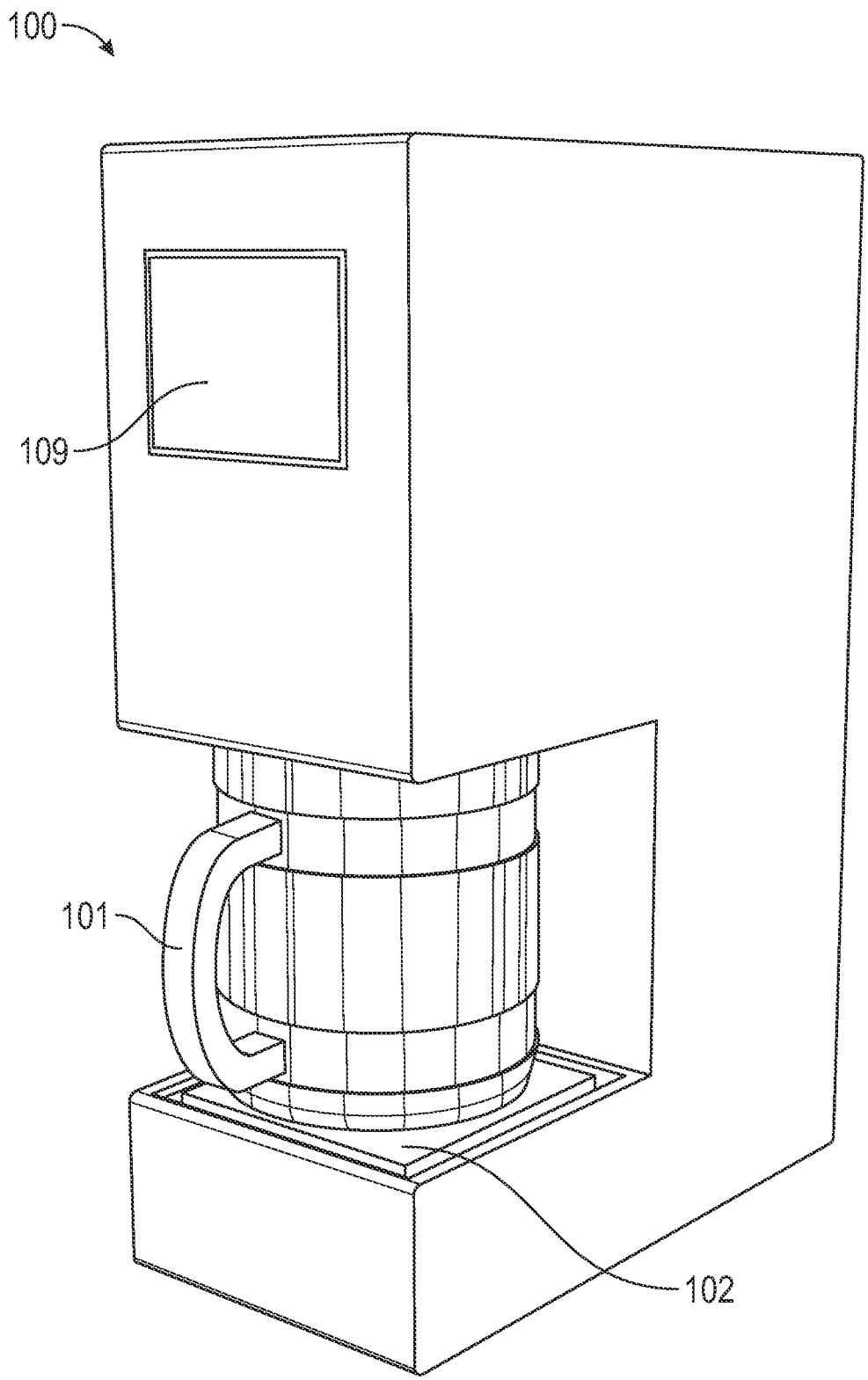
FIG. 1 is a perspective view of an oil extraction apparatus, in accordance with the present disclosure.

Referring to FIG. 1, an oil extraction apparatus 100 is shown. In some aspects, the oil extraction apparatus 100 is of dimensions fit for placement on a countertop, and is therefore suitable for home use. According to an exemplary embodiment, the oil extraction apparatus 100 includes a vessel 101 and a heater assembly 102. The vessel 101 is configured to receive raw plant material and ethanol. The vessel 101 is in contact with the heater assembly 102. In some aspects, the vessel 101 is a glass jug. In some aspects, the vessel 101 has a lid 103 on top of it. The lid 103 may form an air-tight seal at an upper portion of the vessel 101. The lid 103 may include an orifice 104 in fluid communication with a socket 105, such as a Teflon® socket. The combination of the lid 103 and Teflon® socket 105 create a pathway (e.g., an airtight pathway) for removal of evaporated ethanol from the vessel 101 to a reclamation vessel 106. The Teflon® socket 105 connects with a cooling assembly 107 and allows for removal of evaporated ethanol from the vessel 101. The lid 103 can allow the pressure within the vessel 101 to be modified, as desired, such as to modify the heat of vaporization or the melting points of contents in the vessel 101. In some aspects, the heater assembly 102 is a heating mantle or hot plate. In some aspects, the heater assembly 102 sits atop a wiring compartment 108. The wiring compartment 108 is configured to house electric wiring. The temperature of a heating element of the heater assembly 102 may be controlled, as desired, such as by adjusting a temperature of the electric wiring.

The vessel 101 receives raw plant material, such as hemp including CBD oil therein. According to an exemplary embodiment, the vessel 101 receives an effective amount of raw plant material and an effective amount of ethanol. In some aspects, the vessel 101 receives approximately 50 mL of solvent and approximately 7 grams of hemp material. For example, solvent may include ethanol, a water-ethanol mixture, cryogenic ethanol, glycerin, or over-proof alcohol, among other organic solvents.

In accordance with some embodiments, raw hemp material may include extractable CBD oil. For example, hemp material may include full spectrum CBD, broad spectrum CBD, or isolated CBD.

In accordance with some embodiments, extracted oil may include CBD oil and/or THC oil. As an example, CBD oil may be raw, decarboxylated, or filtered, among other types. Raw CBD oil is not processed other than some original extraction before using an oil extraction apparatus. Raw CBD oil may include other compounds such as, for example, small plant materials, lipids, fats, waxes, chlorophyll, and terpenes, among other compounds. Raw hemp extracts may contain a high concentration of CBD. Decarboxylated CBD oil is CBD oil that has undergone a reaction of decarboxylation. Decarboxylation is the process that activates compounds in cannabis, such as THC (tetrahydrocannabinol), among other things.

In accordance with some embodiments, the heater assembly 102 is set to a temperature of approximately 60 degrees centigrade.

Figure 2:
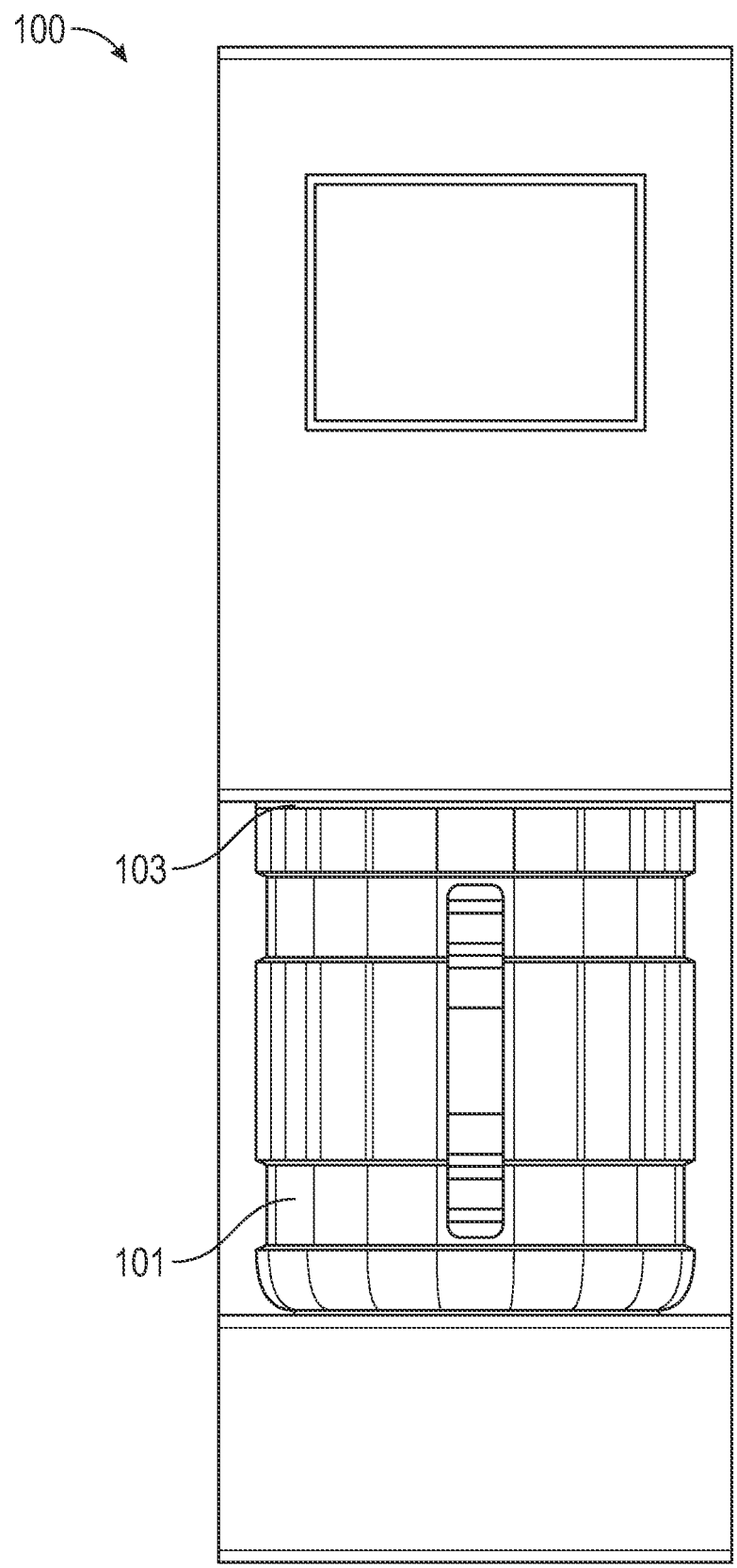
FIG. 2 is a front view of the oil extraction apparatus of FIG. 1, in accordance with the present disclosure.

Referring to FIGS. 1 and 2, the oil extraction apparatus 100 includes an LCD or LED touchscreen interface 109, as an example. The touchscreen interface 109 may be programmed with a plurality of settings to activate the ultrasonic extraction. For example, a first setting may be programmed to activate ultrasonic extraction to yield a higher or lower concentration of extracted ultrasonicated solution of raw material and oil than a second setting or subsequent setting. In some embodiments, the touchscreen interface 109 may be programmed to a user's desired specifications.

Figure 3:
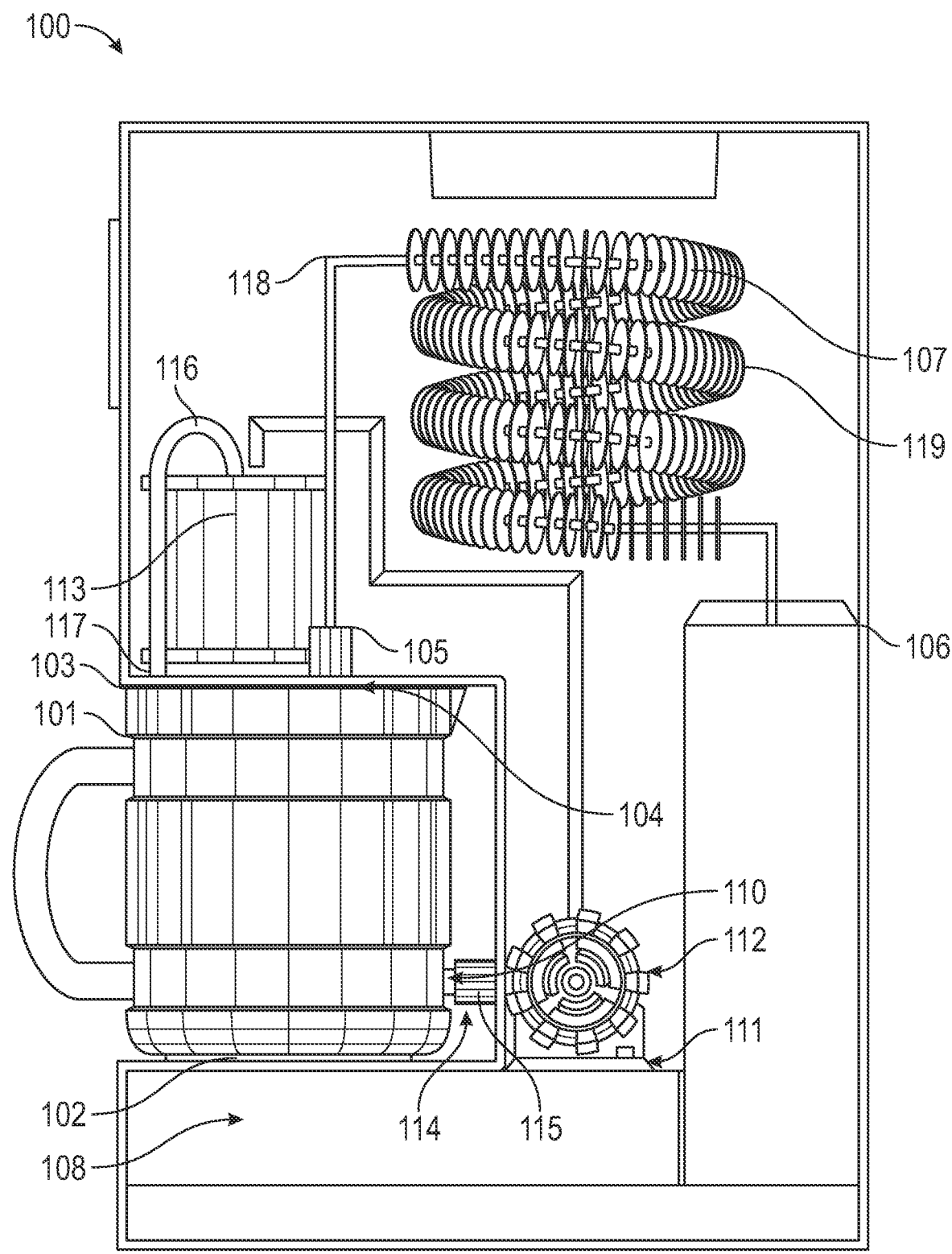
FIG. 3 is an internal side view of the oil extraction apparatus of FIG. 1, in accordance with the present disclosure.
Figure 4:
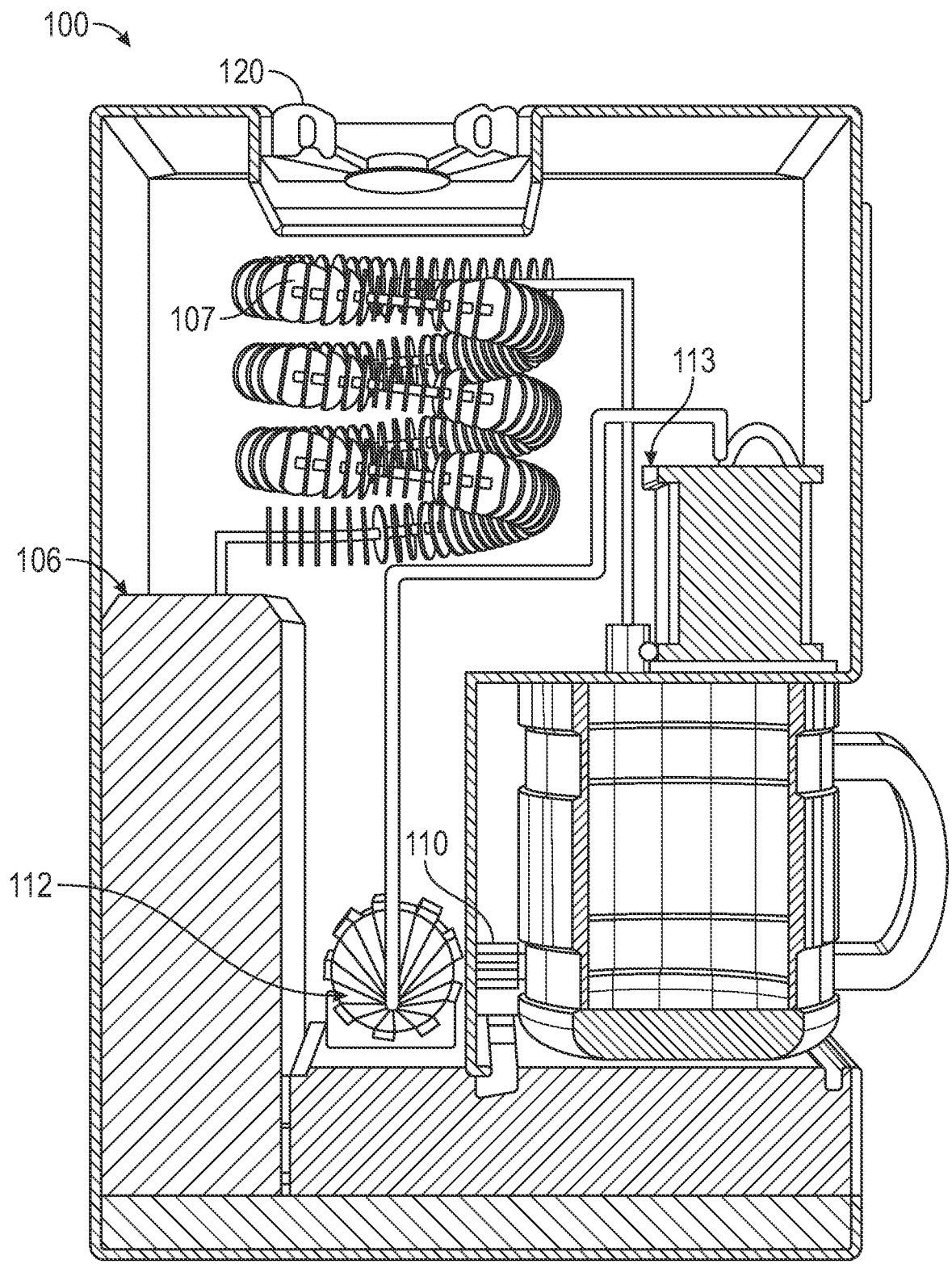
FIG. 4 is a cross-sectional view of the oil extraction apparatus of FIG. 1, in accordance with the present disclosure.
Figure 5:
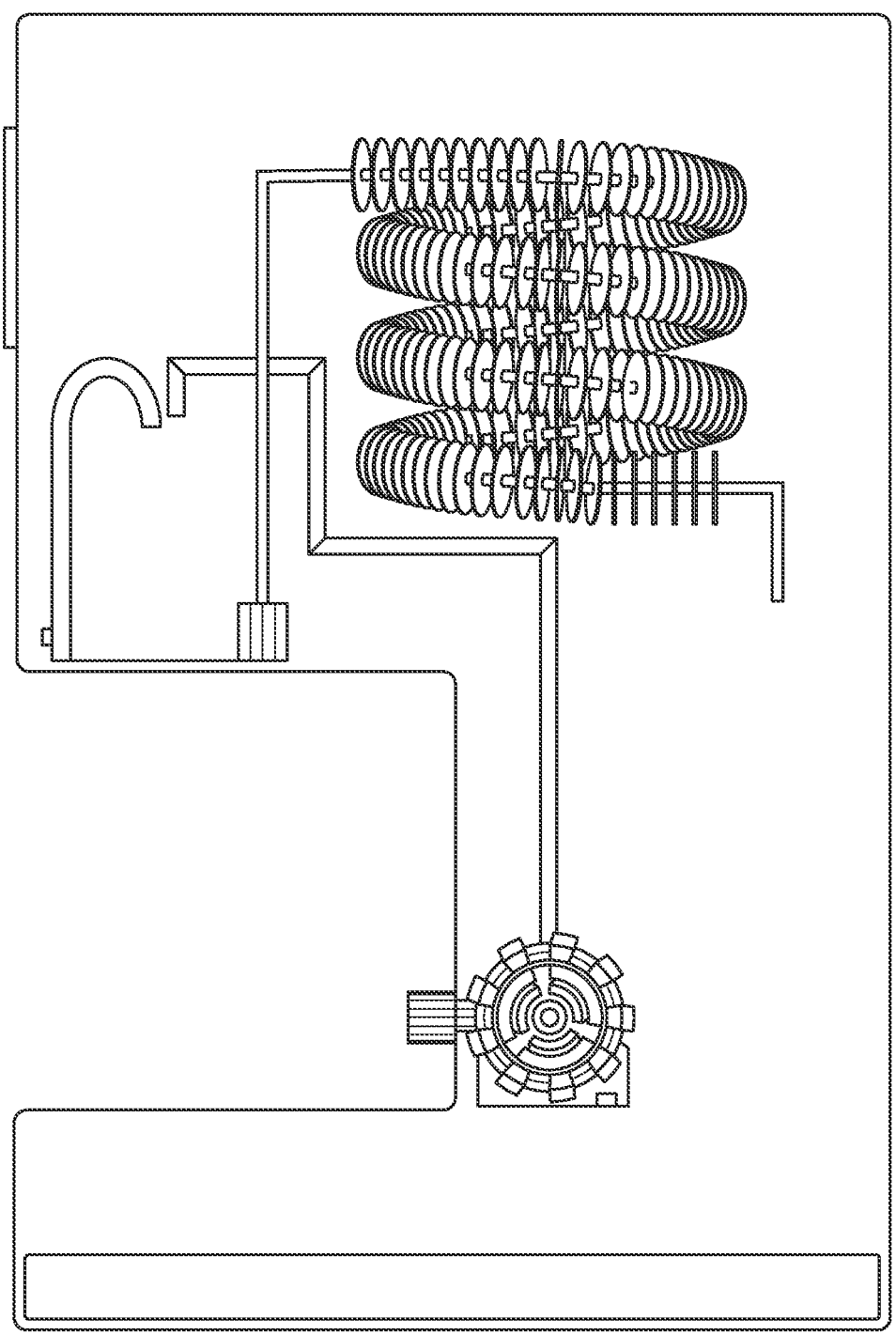
FIG. 5 is a side view of the oil extraction apparatus of FIG. 1, in accordance with the present disclosure.

Referring to FIGS. 3-5, side views of the inner components of the oil extraction apparatus 100 are shown. In some aspects, the oil extraction apparatus 100 includes an ultrasonic transducer 110. The ultrasonic transducer 110 is configured to ultrasonicate the raw plant material received in the vessel 101. Ultrasonication creates alternating low-pressure and high-pressure waves in liquids. In accordance with some embodiments, ultrasonication takes approximately 15 minutes to complete. Ultrasonication has been found by the inventors to act as an effective method for lysing plant cells, and extracting contents of the raw plant materials to generate extracted CBD oil therefrom.

In accordance with some embodiments, the ultrasonic transducer 110 is a probe. In some aspects, the probe generates or receives ultrasonic vibrations. In some aspects, the probe converts electrical energy to ultrasonic energy. In some aspects, the ultrasonic transducer is a bath. In some aspects, the bath spreads energy diffusely over a relatively large volume.

According to an exemplary embodiment, the ultrasonic transducer 110 is part of a quick-connect assembly 111. In some aspects, the quick-connect assembly 111 is in fluid communication with the vessel 101.

According to an exemplary embodiment, the oil extraction apparatus 100 includes a pump 112. The pump 112 is configured to transport a mixture from the vessel 101, the mixture including ethanol and the ultrasonicated raw plant material. In some aspects, the pump 112 may be a positive displacement pump, such as a vane pump or a peristaltic pump, as an example. For example, a peristaltic pump may be a hose pump or a tube pump.

According to an exemplary embodiment, the oil extraction apparatus 100 includes a filter 113. The filter 113 is in fluid communication with the pump 112 and receives the mixture from the pump 112. A coupling connection 114 is between the vessel and the filter. In some aspects, the coupling connection includes a Teflon® socket 115. As an example, the Teflon® socket 115 is in fluid communication with the vessel 101, such as with the lid 103 of the vessel 101.

According to an exemplary embodiment, the oil extraction apparatus 100 includes stainless-steel tubing 116. The stainless-steel tubing 116 extends from the filter 113 to the vessel 101. In some aspects, the stainless-steel tubing 116 includes a pressure-relief valve 117. In some aspects, the stainless-steel tubing 116 circulates excess solvent from the mixture.

According to an exemplary embodiment, the oil extraction apparatus 100 includes copper tubing 118. The copper tubing 118 extends from the vessel 101. In some aspects, the copper tubing 118 transports evaporated ethanol generated by heating the vessel 101 to a reclamation vessel 106.

According to an exemplary embodiment, the oil extraction apparatus 100 includes the cooling assembly 107. The cooling assembly 107 may include a plurality of aluminum fans 119. The plurality of aluminum fans 119 are configured to circumferentially surround the copper tubing 118. According to an exemplary embodiment, the cooling assembly 107 is configured to use air from the plurality of aluminum fans 119 to cool the apparatus and recover solvent and ethanol.

According to an exemplary embodiment, the oil extraction apparatus 100 includes the reclamation vessel 106. The cooling assembly 107 is in fluid communication with the reclamation vessel 106. According to an exemplary embodiment, the reclamation vessel 106 receives evaporated ethanol from the vessel 101 and transported by the cooling assembly 107.

In some aspects, approximately 1000 mg of CBD may be extracted. For example, the approximately 1000 mg of CBD may be used to create, or in combination with, among other things, beauty products—such as soaps, toners, bath bombs, shampoos and conditioners, and lip balms—concentrates, drinks—such as powdered drink mixes and energy shots—edibles, pet products, suppositories, topicals, transdermal patches, water-soluble or emulsified CBD, medium-chain triglycerides (MCT) oil, vape products—such as disposable vape pens, vape cartridges, and vape oil—butter, coconut oil, oil-based capsules or oil-based tinctures.

In accordance with some embodiments, the oil extraction process takes approximately 40-50 minutes to complete after ultrasonication.

Figure 6:
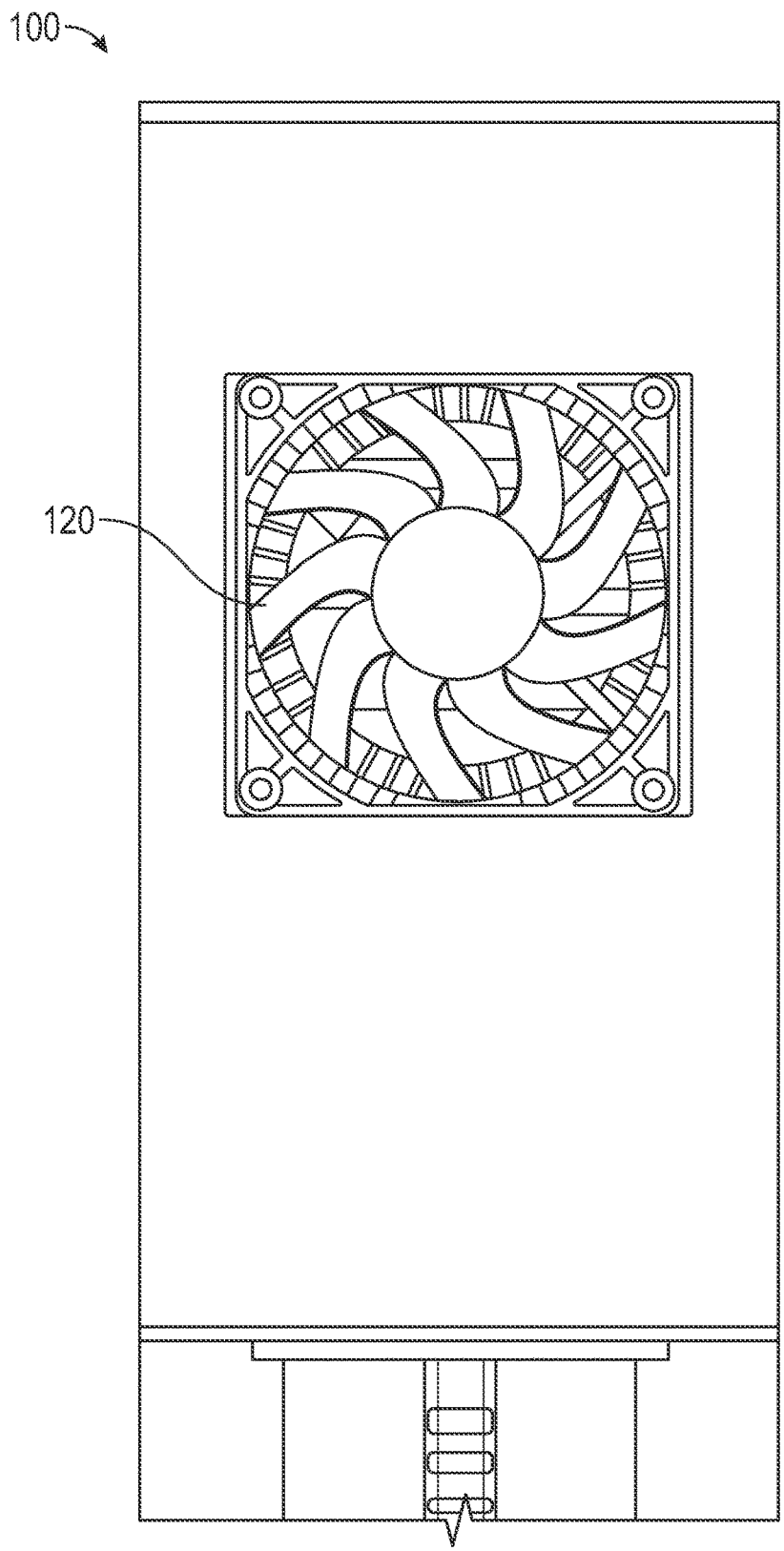
FIG. 6 is a top plan view of the oil extraction apparatus of FIG. 1, in accordance with the present disclosure.

Referring to FIG. 6, a top view of the oil extraction apparatus 100 is shown. The oil extraction apparatus 100 includes an exhaust fan 120. The exhaust fan 120 is configured to remove heat from the apparatus. In some aspects, the exhaust fan 120 is configured to remove vapors from the apparatus.

In some aspects, the filter 113 includes a stainless-steel mesh filtration system.

According to an exemplary embodiment, a method of oil extraction is described. The method of oil extraction includes placing raw plant material in the vessel 101. As an example, an effective amount of ethanol and an effective amount of hemp material are added to the vessel 101. The vessel 101 including raw material is placed on a heater assembly 102.

According to an exemplary embodiment, the method of oil extraction includes selecting a program on an LCD or LED touchscreen interface 109. The touchscreen interface 109 may be programmed with a plurality of settings to activate ultrasonic extraction. For example, a first setting may be programmed to activate ultrasonic extraction to yield a higher or lower concentration of extracted ultrasonicated solution of raw material and oil than a second setting or subsequent setting. In some embodiments, the touchscreen interface 109 may be programmed to the user's desired specifications.

According to an exemplary embodiment, the method of oil extraction includes heating the heater assembly to approximately 60 degrees centigrade.

Figure 7:
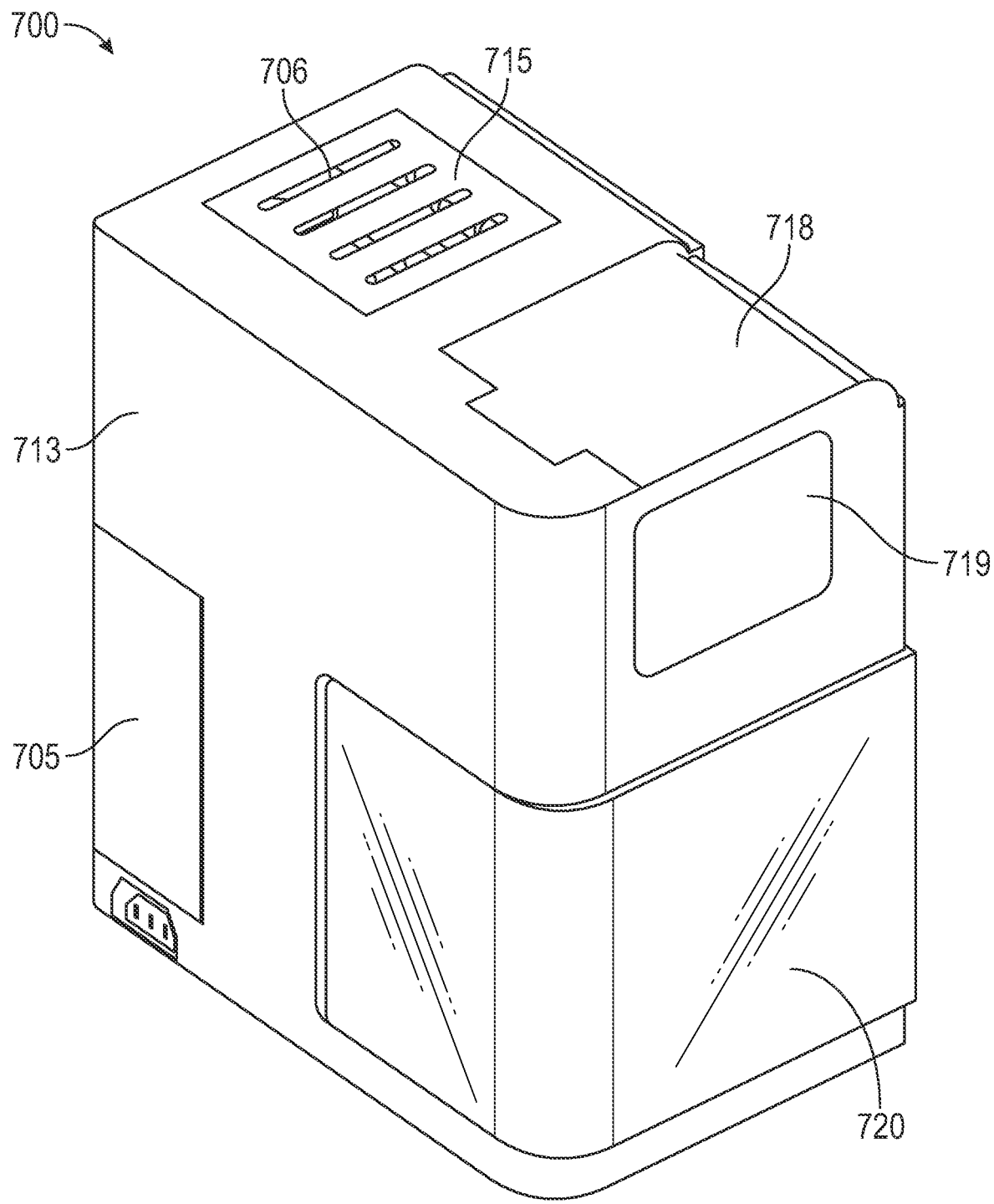
FIG. 7 is a perspective view of an oil extraction apparatus, in accordance with the present disclosure.
Figure 8:
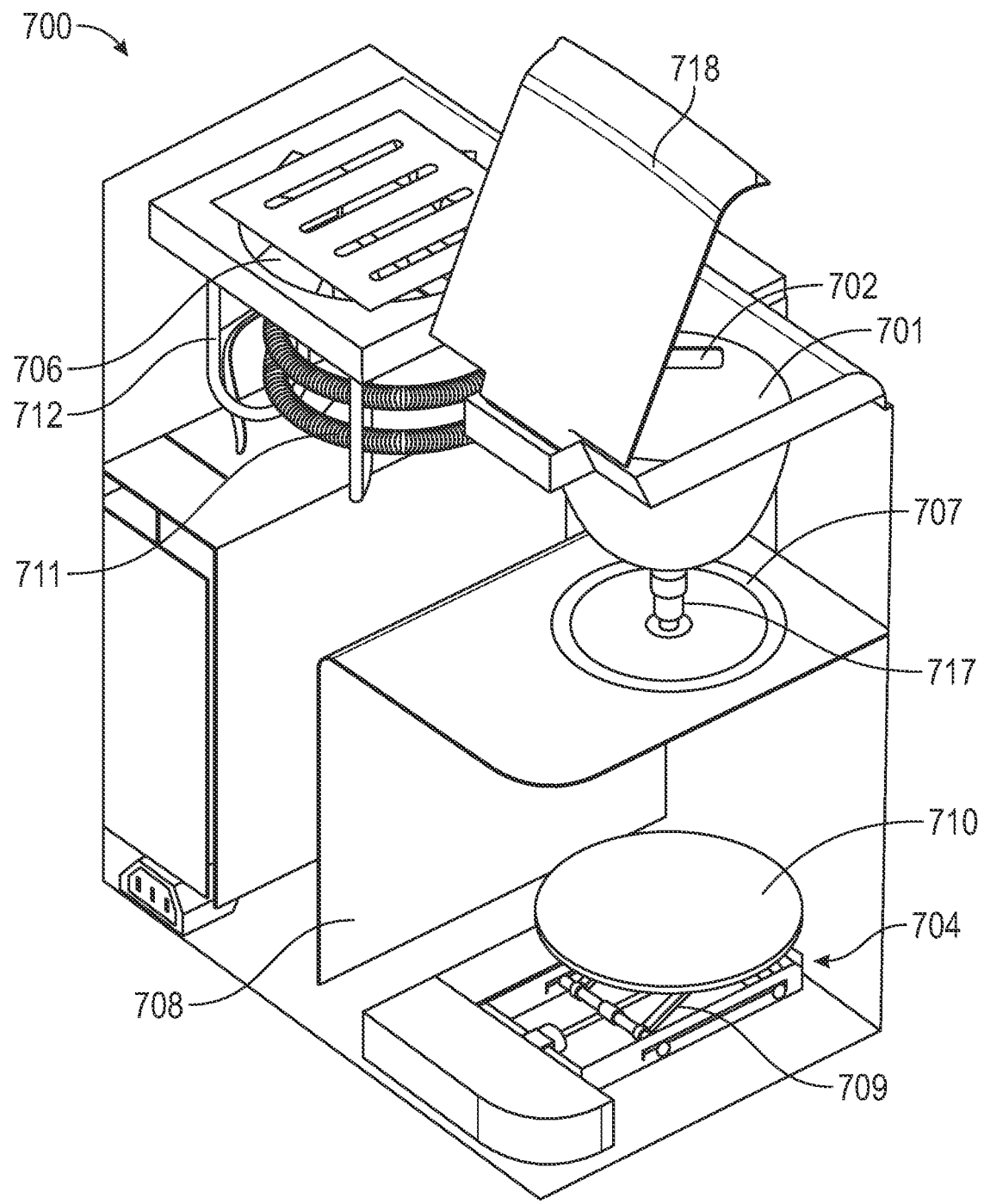
FIG. 8 is an internal, perspective view of the oil extraction apparatus of FIG. 7.
Figure 9:
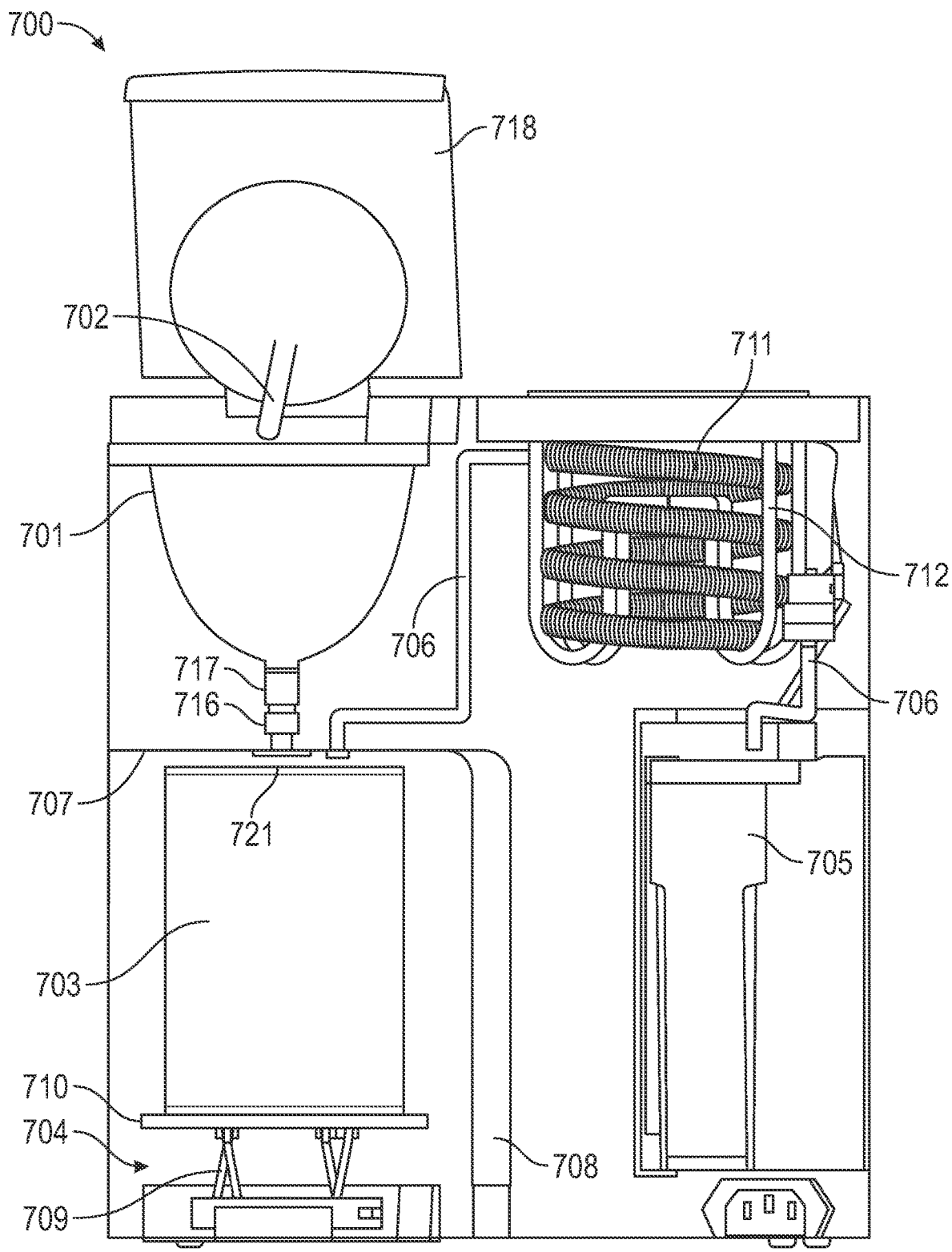
FIG. 9 is an internal, side view of the oil extraction apparatus of FIG. 7.

Referring to FIGS. 7-9, oil extraction apparatus 700 includes an ultrasonication vessel 701 that receives raw plant material and ethanol. An ultrasonication probe 702 is configured to be positioned in the ultrasonication vessel 701. The ultrasonication probe 702 is configured to ultrasonicate the raw plant material received in the ultrasonication vessel 701 and generate a mixture including ultrasonicated raw plant material, plant oil, and ethanol. A collection vessel 703 is in fluid communication with the ultrasonication vessel 701. The collection vessel 703 receives a mixture including plant oil and ethanol from the ultrasonication vessel 701. A heater heats 704 the collection vessel 703 to separate ethanol from the mixture including plant oil and ethanol. A reclamation vessel 705 is in fluid communication with the collection vessel 703. The reclamation vessel 705 receives separated ethanol from the mixture including plant oil and ethanol. An ethanol collection tube 706 is connected with the reclamation vessel 705. The ethanol collection tube 706 is arranged to carry separated ethanol from the mixture including plant oil and ethanol to the reclamation vessel 705 from the collection vessel 703.

In use, the heater 704 vaporizes ethanol in the mixture including plant oil and ethanol to separate ethanol from the mixture to generate purified plant oil (e.g., CBD oil of a desired volume and/or a desired concentration). The ethanol is vaporized by the heater 704 (while the oil remains in liquid form) and is carried through at least a portion of the ethanol collection tube 706 as ethanol vapor. That is, as the ethanol vapor passes through the ethanol collection tube 706 it can be cooled and converted back into liquid ethanol for collection in the reclamation vessel 705. The reclaimed liquid ethanol can therefore be recycled and reused for a later oil extraction process. This increases the efficiency of operation of the oil extraction apparatus 700 and reduces operating costs.

The heater 704 may be in direct contact with the collection vessel 703 (e.g., with a bottom surface of the collection vessel 703).

In some aspects, a sealing membrane 707 is arranged between the ethanol collection tube 706 and the collection vessel 703. The sealing membrane 707 forms an airtight seal between the ethanol collection tube 706 and the collection vessel 703. The sealing membrane 707 may be positioned within a wall of housing 708. Housing 708 may be disposed within the oil extraction apparatus 700 to separate the collection vessel 703 from the other components of oil extraction apparatus 700. Alternatively, the sealing membrane 707 may be positioned above or below housing 708. The sealing membrane 707 is arranged to directly contact an upper portion of the collection vessel 703 to form the airtight seal. The sealing membrane 707 may be spring loaded (e.g., via a compression arm extending downward from the ultrasonication vessel 701) to allow a degree of upward or downward movement with respect to the housing 708 for forming and maintaining the airtight seal with the collection vessel 703.

In some aspects, a lift 709 is arranged adjacent the collection vessel 703 (e.g., directly below the collection vessel 703). The lift 709 is configured to apply pressure between the collection vessel 703 and the collection tube 706 to form the aright seal between the collection tube 706 and the collection vessel 703. As an example, the lift 709 can apply upward pressure between an upper portion of the collection vessel 703 and the sealing membrane 707.

In some aspects, the heater 704 includes a heating plate 710. The lift 709 is configured to apply pressure to the heating plate 710 to form the airtight seal between the collection tube 706 and the collection vessel 703 (e.g., while the collection vessel 703 is being heated by the heater 704).

As an example, the lift may be a mechanical lift or a hydraulic lift. The mechanical lift may be a scissor lift.

A cooling coil 711 is arranged around at least a portion of the ethanol collection tube 706. The cooling coil 711 is configured to convert ethanol vapor to liquid ethanol. The cooling coil 711 may include copper or aluminum. The cooling coil 711 is supported by support arms 712 extending from housing 713. Heat may also be dissipated through vent 714. A fan, such as the fan 120 described above, may be arranged below vent 714 for dissipating heat from the housing 713. Vent 714 is covered by vent cover 715.

In some aspects, the ultrasonication vessel 701 defines a cone shape. A filter 716 is arranged between the ultrasonication vessel 701 and the collection vessel 703. The filter 716 is configured to prevent ultrasonicated raw plant material from entering the collection vessel 703. A check valve 717 is arranged between the ultrasonication vessel 701 and the collection vessel 703. The check valve 717 is configured to be opened after the ultrasonication of the raw plant material is completed to extract plant oil from the raw plant material to pass plant oil and ethanol to the collection vessel 703.

In some aspects, a lid 718 of the oil extraction apparatus 700 supports the ultrasonication probe 702. The ultrasonication probe 702 can be removably positioned in the ultrasonication vessel 701 by closing the lid 718 and removed from the ultrasonication vessel 701 by opening the lid 718.

Housing 713 includes LCD panel 719 and access door 720. Access door 720 allows a user to access and/or enclose the collection vessel 703 (e.g., during use of the oil extraction apparatus 700).

In some aspects, the collection vessel 703 includes an airtight lid 721. The airtight lid 721 is configured to form an airtight seal between the collection vessel 703 and the ethanol collection tube 706.

Figure 10:
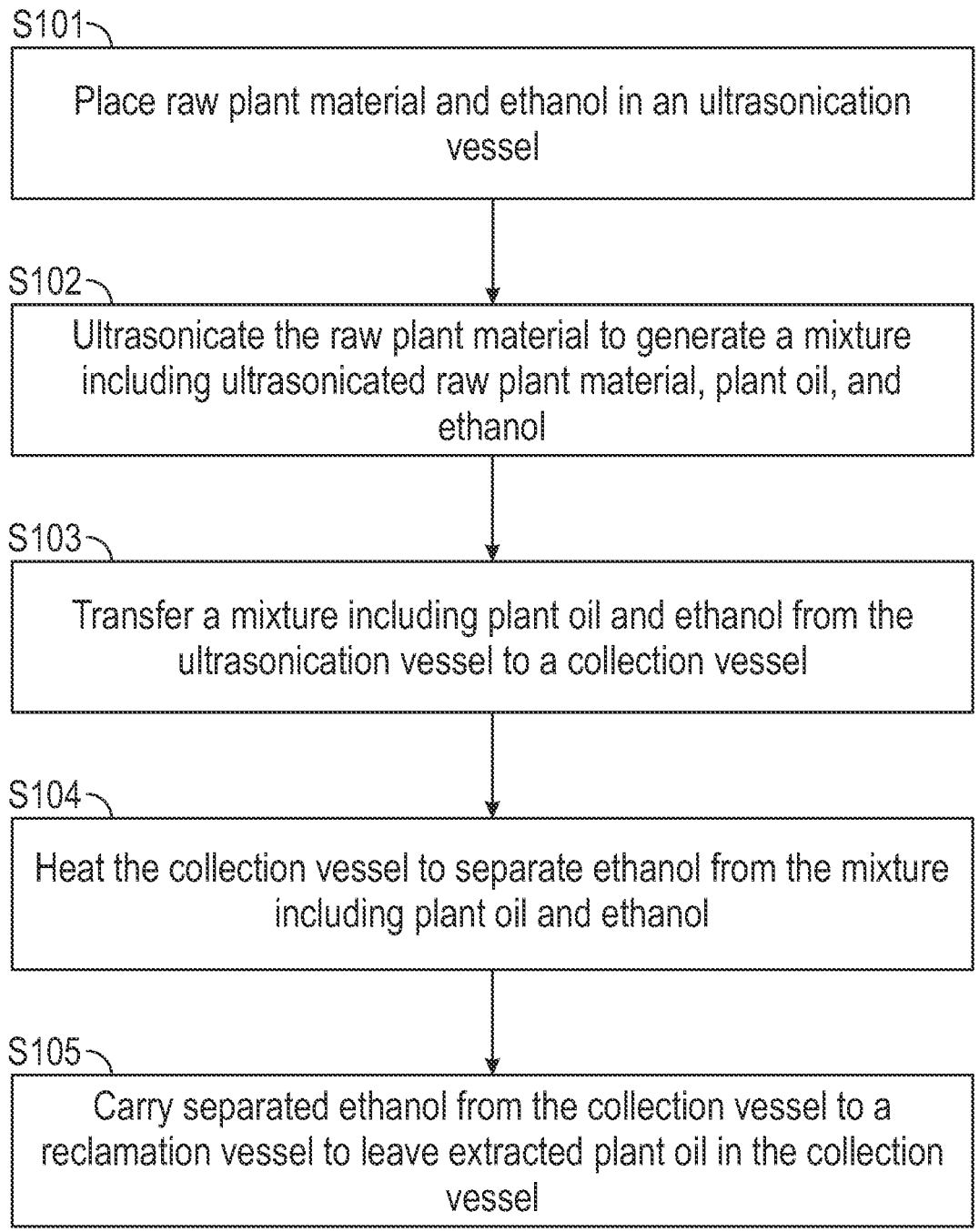
FIG. 10 is a flow chart of a method of extracting oil in accordance with the present disclosure.

Referring to FIG. 10, a method of oil extraction includes placing raw planter material and ethanol in an ultrasonication vessel (step S101). The raw plant material is ultrasonicated to generate a mixture including ultrasonicated raw plant material, plant oil, and ethanol (step S102). A mixture including plant oil and ethanol is transferred from the ultrasonication vessel to a collection vessel (step S103). The collection vessel is heated to separate ethanol from the mixture including plant oil and ethanol (step S104). The separated ethanol transferred from the collection vessel to a reclamation vessel to leave extracted plant oil in the collection vessel (step S105).

The ultrasonicated raw plant material is filtered out of the mixture (e.g., by a mesh filter positioned in check valve) as the plant oil and ethanol are transferred to the collection vessel 703.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. An oil extraction apparatus, comprising:
an ultrasonication vessel configured to receive raw plant material and ethanol;
an ultrasonication probe configured to be positioned in the ultrasonication vessel, the ultrasonication probe configured to ultrasonicate the raw plant material received in the ultrasonication vessel and generate a mixture including ultrasonicated raw plant material, plant oil, and ethanol;

a collection vessel in fluid communication with the ultrasonication vessel, the collection vessel configured to receive a mixture including plant oil and ethanol from the ultrasonication vessel;

a heater configured to heat the collection vessel to separate ethanol from the mixture including plant oil and ethanol;

a reclamation vessel in fluid communication with the collection vessel, the reclamation vessel configured to receive separated ethanol from the mixture including plant oil and ethanol; and an ethanol collection tube connected with the reclamation vessel, the ethanol collection tube arranged to carry separated ethanol from the mixture including plant oil and ethanol to the reclamation vessel from the collection vessel.

2. The oil extraction apparatus of claim 1, further including a sealing membrane arranged between the ethanol collection tube and the collection vessel, the sealing membrane configured to form an airtight seal between the ethanol collection tube and the collection vessel.

3. The oil extraction apparatus of claim 2, wherein the heater is configured to vaporize ethanol in the mixture including plant oil and ethanol, and wherein ethanol is carried through at least a portion of the ethanol collection tube as ethanol vapor.

4. The oil extraction apparatus of claim 3, further including a lift arranged adjacent the collection vessel, the lift configured to apply pressure between the collection vessel and the collection tube to form the aright seal between the collection tube and the collection vessel.

5. The oil extraction apparatus of claim 4, wherein the heater includes a heating plate, and wherein the lift is configured to apply pressure to the heating plate to form the airtight seal between the collection tube and the collection vessel.

6. The oil extraction apparatus of claim 4, wherein the lift is a mechanical lift or a hydraulic lift.

7. The oil extraction apparatus of claim 6, wherein the mechanical lift is a scissor lift.

8. The oil extraction apparatus of claim 4, further including a cooling coil arranged around at least a portion of the ethanol collection tube, the cooling coil configured to convert ethanol vapor to liquid ethanol.

9. The oil extraction apparatus of claim 8, wherein the cooling coil includes copper or aluminum.

10. The oil extraction apparatus of claim 4, wherein the ultrasonication vessel defines a cone shape.

11. The oil extraction apparatus of claim 10, further including a filter arranged between the ultrasonication vessel and the collection vessel, the filter configured to prevent ultrasonicated raw plant material from entering the collection vessel.

12. The oil extraction apparatus of claim 11, further including a check valve arranged between the ultrasonication vessel and the collection vessel.

13. The oil extraction apparatus of claim 1, further including a housing arranged between the ethanol collection tube and the collection vessel, the housing configured to form an airtight seal between the collection tube and the collection vessel.

14. The oil extraction apparatus of claim 1, further including a fan configured to remove heat generated by the heater.

15. The oil extraction apparatus of claim 1, further including a lid supporting the ultrasonication probe, wherein the ultrasonication probe is configured to be removably positioned in the ultrasonication vessel by closing the lid.

16. The oil extraction apparatus of claim 1, further including an airtight lid removably disposed on the collection vessel, the airtight lid configured to form an airtight seal between the collection vessel and the ethanol collection tube.

17. The oil extraction apparatus of claim 1, wherein the plant oil includes CBD oil.

18. The oil extraction apparatus of claim 1, wherein the plant oil includes a broad spectrum CBD extract.

* * * * *